(12) United States Patent
Lacouture

(10) Patent No.: US 6,390,089 B1
(45) Date of Patent: May 21, 2002

(54) NOSTRIL EXPANSION DEVICE WITH INTERCHANGEABLE COMPONENTS

(76) Inventor: Michael Lacouture, 2630 Wanda, Simi Valley, CA (US) 93065

(*) Notice: Subject to any disclaimer, the term of this patent is extended or adjusted under 35 U.S.C. 154(b) by 0 days.

(21) Appl. No.: 09/791,276

(22) Filed: Feb. 23, 2001

(51) Int. Cl.$^7$ .............................................. A61M 15/00
(52) U.S. Cl. .................. 128/200.24; 128/848; 602/902; 606/204.45
(58) Field of Search ............................ 128/200, 200.4, 128/207.18, 848, DIG. 26, 200.24; 602/41, 52, 54–60, 74, 902; 600/220; 606/1, 198–199, 201, 204.45

(56) References Cited

U.S. PATENT DOCUMENTS

| | | | |
|---|---|---|---|
| 4,201,217 A | * | 5/1980 | Slater .......................... 606/199 |
| 5,890,486 A | * | 4/1999 | Mitra et al. ............ 128/200.24 |
| 6,196,228 B1 | * | 3/2001 | Kreitzer et al. ............. 128/848 |
| 6,238,411 B1 | * | 5/2001 | Thorner ...................... 606/199 |

* cited by examiner

Primary Examiner—Michael A. Brown
Assistant Examiner—Lalitaa M. Hamilton
(74) Attorney, Agent, or Firm—Goldstein Law Offices

(57) ABSTRACT

A nostril expansion system, for use on a nose having a bridge and nostrils, comprising a pair of pads and a clip. The clip has a pair of ends which each detachably mount to one of the pads. The pads have an outer periphery and a central portion. Adhesive is located on the central portion for adhering the pad to the nostril. The outer periphery has no adhesive and has a serrated edge to facilitate removal of the pad from the nostril. Several clips are provided to allow the user to select a more comfortable fit according to the user's nasal condition.

10 Claims, 2 Drawing Sheets

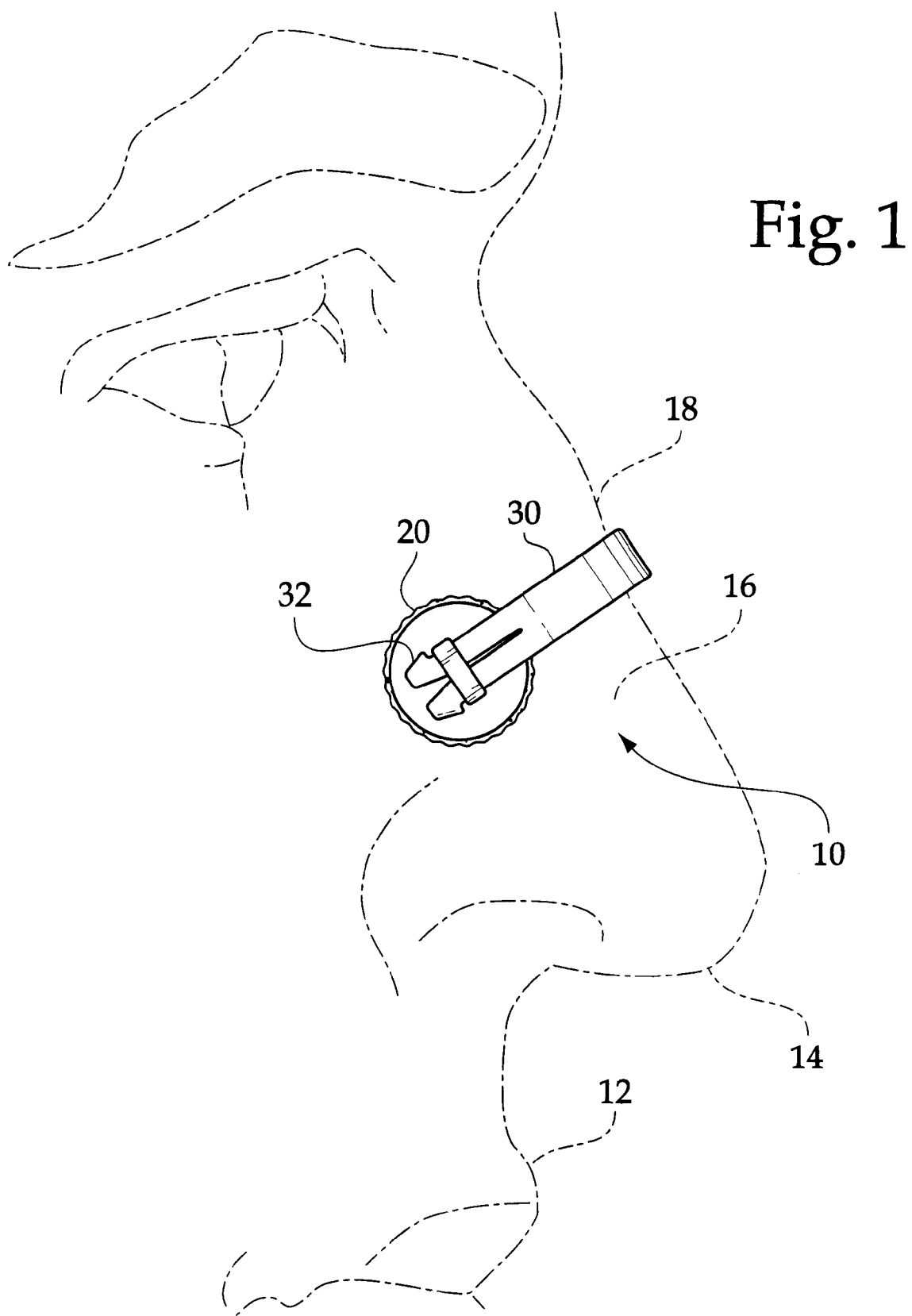

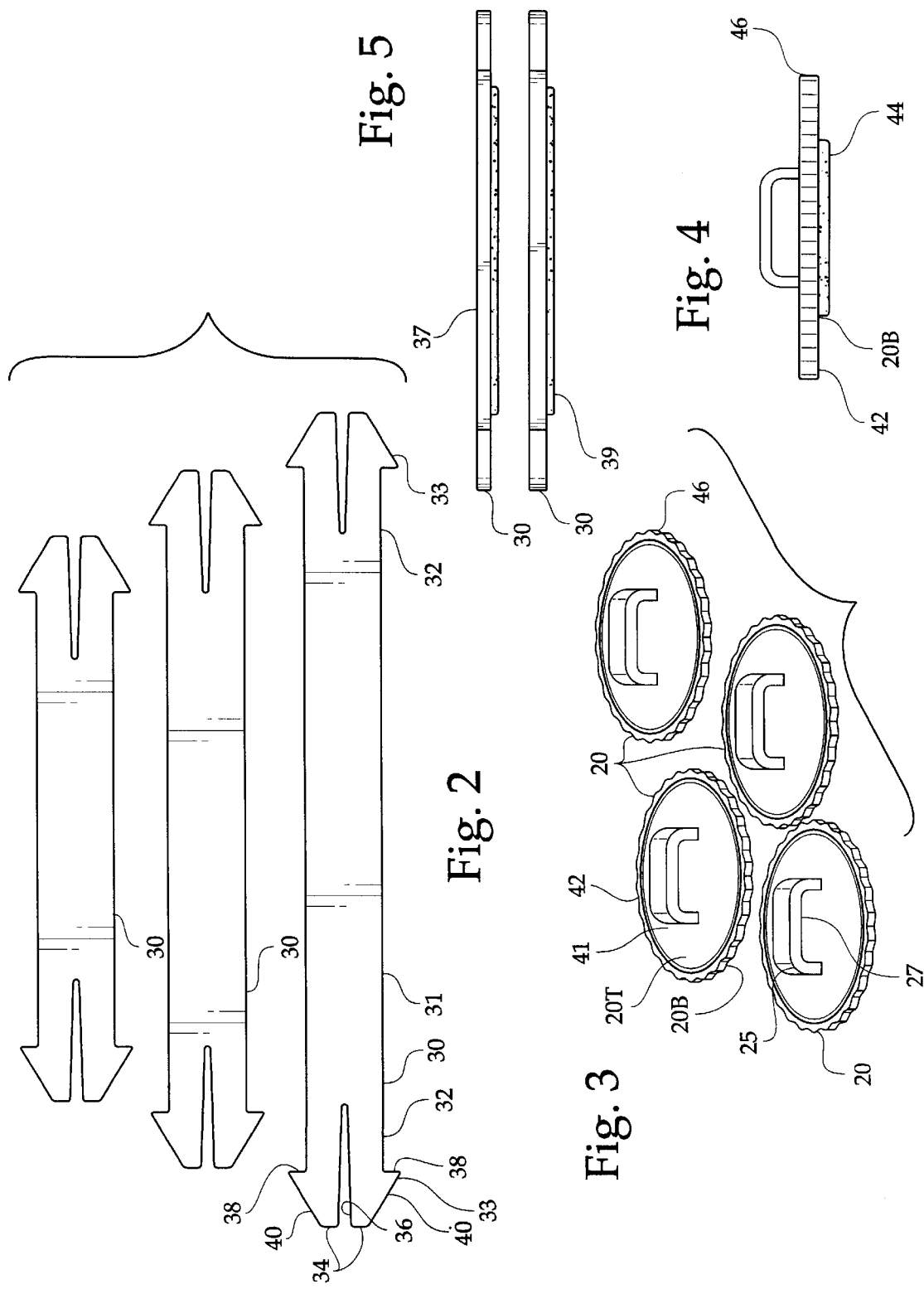

NOSTRIL EXPANSION DEVICE WITH INTERCHANGEABLE COMPONENTS

BACKGROUND OF THE INVENTION

The invention relates to a nostril expansion device. More particularly, the invention relates to a nostril expansion device which employs changeable pads and clips which may selectable and interchanged by the user to achieve effective nostril expansion while providing simultaneous comfort and allowing repeated use.

A variety of conditions make it difficult for a person to breathe through their nose. Decreased air passage through the nose can have a variety of effects on an individual, ranging from discomfort to snoring. A variety of chemical (drug) treatments are available which seek to treat many of these ailments, and open nasal passages. Such treatments vary in effectiveness. However primitive it may seem, mechanically holding the nostrils in the open position is the only effective solution for some. In addition, mechanically opening the nostrils eliminates side effects commonly associated with drug therapy.

Mechanical nasal expanders have been attempted in various configurations over the past century. In particular, U.S. Pat. No. 1,292,083 to Sawyer discloses a device which attaches to the nostrils, and uses a stiff wire to urge the nostrils outward.

Later attempts generally were configured as one piece, tape-like constructions which extended from one nostril, along the surface of the nose, across the bridge, to the other nostril. For example, U.S. Pat. Nos. 5,609,150 to Maged; 5,718,224 to Muchin; 5,806,525 to Pope; 5,884,628 to Hilsen; 5,890,486 to Mitra et al.; and Re. 35,408 to Petruson all disclose devices having this general configuration.

One further device is the subject of U.S. Pat. No. 5,476,091 to Johnson, sold under the trade name BREATHRIGHT. Johnson employs a pair of resilient bands, embodied within a multi-layered, tape like construction.

While these units may be suitable for the particular purpose employed, or for general use, they would not be as suitable for the purposes of the present invention as disclosed hereafter.

SUMMARY OF THE INVENTION

It is an object of the invention to provide a device which effectively dilates the nostrils so as to open nasal passages and allow natural breathing to occur therethrough. Accordingly, the device engages the nostrils and pulls them outward to mechanically effect dilation of the nostrils.

It is another object of the invention to provide a device which may be adjusted to accommodate different size noses, and may be adjusted according to necessary dilating force. Accordingly, the pads are detachable from the clips, and the clips may be interchanged to accommodate the comfort of the user, accommodate different size noses, and supply the required dilating force.

It is a further object of the invention to provide a device which may be effectively secured onto the outside of the nostrils, will remain securely in place during use, but which may be easily and painlessly removed following use. Accordingly, the pads have adhesive surfaces. Further, only the pads are adhered to the nose. Still further, a non-adhesive serrated edge on the outer periphery of the pads allow the user to easily and painlessly pry the pads from the nostrils.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 1 is a side elevational view, illustrating the nostril expansion device in use, adhered to the nose of a user.

FIG. 2 is a top plan view of a plurality of clips of different sizes, each laid flat.

FIG. 3 is a diagrammatic perspective view of a plurality of pads, ready for engagement with one of the clips.

FIG. 4 is a side elevational view, illustrating that the adhesive located beneath a central portion of one of the pads, wherein no adhesive is located beneath the outer serrated edge.

FIG. 5 is a side elevational view of two clips according to the present invention, showing a preferred two layer construction, and showing different clip thicknesses which are used to achieve different expansion strengths.

DETAILED DESCRIPTION OF THE PREFERRED EMBODIMENTS

FIG. 1 illustrates a nostril expansion device 10, in use by a user 12. The user 12 has a nose 14, including a pair of nostril outer surfaces 16 and a bridge 18. The expansion device 10 comprises a pair of pads 20 (one is shown), and a clip 30 which extends between the pads 20. More particularly, the clip 30 has a pair of ends 32, and each pad 20 is removably mated with one of the ends 32 of the clip 10. As illustrated in FIG. 1, the pads 20 are each adhered to one of the nostril outer surfaces 16, and the clip 30 extends over the bridge 18. When in use, the clip 30 is flexed to a position wherein its ends 32 extend nearly parallel to each other and pointed in the same direction. In this flexed position, the clip 30 has a natural tendency to return to a flat position, wherein the ends 32 are substantially planar and point in opposite directions. Accordingly the clip 30 has a spring force which exerts a force perpendicular to the nostril outer surface 16, providing a tendency to dilate or expand the nostril and open air passages therein.

Referring to FIG. 2, several clips 30 are shown laid flat. The clips 30 are preferably made of a flexible plastic, and may include a clear plastic upper layer, over a skin-colored fabric. The various clips 30 are different sizes, for accommodating different size users. In addition, the clips 30 may be made to have different strengths. That is, by selecting the materials and thickness of the clips 30, the actual spring force exerted by the clips 30 may be varied. Accordingly a weaker clip may be used for a less severe nasal condition, while a strong clip may be required when more significant dilation is required.

FIG. 5 is a side elevational view of two of the clips, laid flat. In FIG. 5 it is apparent that the clips have different thicknesses. As previously indicated, varying the thickness of the clip 30 will vary it's "strength", by varying the spring force it will exert against the pads when attached thereto. Also apparent in FIG. 5, is that the clip 30 has an upper layer 37 of plastic (preferably clear plastic), and a lower layer of fabric 39 (preferably skin-colored fabric). This combination contributes to both the comfort and unobtrusiveness of the device.

Referring again to FIG. 2, the ends 32 of each clip are configured to detachably mate with the pads 20. Referring momentarily to FIG. 3, the pads 20 each have a pad ring 25, which defines a pad ring opening 27, having an opening width extending laterally across the pad 20. Accordingly, the clip has a main portion 31 and a catch assembly 33 at each of the two ends 32. The main portion 31 has a width which is substantially equivalent to the opening 27 in the pad ring 25. In particular, catch assembly 33 comprises a pair of catches 34, separated by a slit 36. Each of the catches has a hook 38, and a ramp 40. As the catch assembly 32 is inserted into the pad ring opening 27, the ramps 40 engage the pad ring 25 and cause the catches 34 to move inward, minimizing the slit 36, until the hook 38 clears the pad ring 25. Once the hook 38 clears the pad ring 25, the catches 34 snap outward, preventing the catch assembly 33 from being removed from the pad ring 25, and thus securing the clip 30 to the pad 20 until removal is desired. To remove the pad 20, the catches 34 are simply urged inward (together) by the user until the hooks 38 span a distance less than the pad ring opening 27, so that the catches 34 can be pulled through the pad ring 25.

Referring now to FIG. 3, the pads have a central portion 41, and an outer perimeter 42. The pads 20 also have a top 20T and a bottom 20B. The pad ring 25 extends from the top 20T. Referring to FIG. 4, adhesive 44 is located beneath the pad 20—in other words, on the bottom 20B. However, the adhesive 44 is only located on the central portion 40. The outer perimeter 42 is devoid of adhesive. In addition, the outer perimeter 42 includes a serrated edge 46. The serrated edge 46 and the lack of adhesive on the outer perimeter 42 together allow for easy removal of the pad 20 from the nose. In particular, the user can easily insert a fingernail beneath the outer perimeter 42 and pry the pad 20 upward to free the adhesive 44 of the central portion 40 from the nose and allow the pad 20 to be removed from the nose.

In use, the user would initially select a clip which best meets the individual needs of the user. In particular, the clip sized to best fit the nose is selected. Among clips of that physical size, the clip which has a suitable strength to meet the dilation needs of the user is selected. That clip is then mated with a pair of pads, and is ready to use. Typically the adhesive on the central portion of the pad would be covered by a "peel-off" protective layer which must be removed prior to use. Following removal of the protective layer, the clip is flexed between the fingers so that the pads extend parallel to each other and directly opposed to each other with their bottom surfaces facing each other. Then, the pads may be adhered directly to the nostrils, with the clip extending over the bridge of the nose. Once the pads have been sufficiently adhered to the nostrils, the clip may be released by the user. Then, the entire tendency of the clip to flex outward is exerted against the nostril outer surfaces. This tendency thereby has a dilating effect on the nostrils, to open the air passages. Once the treatment is complete and the user wishes to remove the device, the user may insert his or her fingernail under the serrated edge of the outer periphery and pry the pad upward. Once the device has been removed from the nose, the clip will un-flex into the flat position, and the catch assemblies may be operated to remove the pads from the clip. The clip may then be reused by adhering two new pads to the clip.

In conclusion, herein is presented a nose expansion device which employs interchangeably clips and pads to achieve effective and comfortable dilation of the nostrils. The invention is illustrated by example in the foregoing description and in the accompanying drawing figures. However, numerous variations are possible while adhering to the inventive concepts. Such variations are contemplated as being a part of the present invention.

What is claimed is:

1. A nostril expansion device, for use on a nose having a bridge and nostrils, comprising:

a pair of pads, the pads each having a central portion and a periphery, the pads having a top and a bottom, a ring located on the top, the ring opening having an opening width, the central portion having adhesive on the bottom, the periphery having no adhesive but having a serrated edge; and a clip having a pair of ends, the clips naturally extending in a flat position where the ends extend in opposite directions, the clip capable of flexing into a position where the two ends extend substantially parallel to each other while oriented in the same direction such that the clip exerts a force that urges the ends away from each other, each of the ends having a catch assembly for detachably mounting to the pads, the catch assembly having a pair of catches which each have a hook, the hooks are fully opposite from each other, the catches are separated by a slit, the catches are capable of bending toward each other, minimizing the slit and shortening a distance between the hooks so that it is less than the opening width of the ring opening so that the catches can be inserted into the ring to accomplish mounting of the pads to the clip.

2. The nostril expansion device as recited in claim 1, further comprising several clips having different thicknesses and numerous pads, such that the pads and clips may be interchanged and detachably connected with each other.

3. The nostril expansion device as recited in claim 2, wherein the clip has a clear plastic upper layer and a fabric lower layer.

4. A nostril expansion device, for use on a nose having a bridge and nostrils, comprising:

a pair of pads, the pads each having a central portion and a periphery, the pads having a top and a bottom, a ring located on the top, the ring opening having an opening width, the pads having adhesive for attaching to the nostrils; and a clip having a pair of ends, the clip ends can be inserted into the ring to accomplish detachable mounting of the pads to the clip, the clip naturally extending in a flat position where the ends extend in opposite directions, the clip capable of flexing into a position where the two ends extend substantially parallel to each other while oriented in the same direction such that the clip exerts an outward force that urges the ends away from each other, such that the clip extends across the bridge of the nose and the outward force of the clips pulls against the nostrils to dilate said nostrils.

5. The nostril expansion device as recited in claim 4, wherein the adhesive is located on the bottom of the central portion, wherein the periphery has no adhesive, and wherein the periphery has a serrated edge which facilitates removal of the pad from the nostril when desired.

6. The nostril expansion device as recited in claim 5, wherein each of the ends of the clip has a catch mechanism, the catch mechanism comprises a pair of catches have a hook, the hooks are fully opposite from each other, the catches are separated by a slit, the catches are capable of bending toward each other, minimizing the slit and shortening a distance between the hooks so that it is less than the opening width of the ring opening so that the catches can be inserted into the ring to accomplish mounting of the pads to the clip.

7. The nostril expansion device as recited in claim 6, further comprising several clips having different thicknesses and numerous pads, such that the pads and clips may be interchanged and detachably connected with each other.

8. The nostril expansion device as recited in claim 7, wherein the clip has a clear plastic upper layer and a fabric lower layer.

9. A nostril expansion method, for use by a user in dilating nostrils of said user, using pads, each pad having a top and a bottom, the top having a pad ring having a pad ring opening, and using clips, the clips having different thicknesses and different spring strengths when flexed, the clips each having a pair of ends which is detachably engageable with the pad ring, comprising the steps of:

a) selecting a clip by the user which has a desired spring strength;

b) mating one pad with each of the ends of said clip;

c) flexing the clip so that the ends extend parallel to each other and in the same direction;

d) adhering the pads to the nostrils of the user;

e) expanding the nostrils by allowing the clip to pull the pads outward against the nostrils by releasing the clip by the user;

f) removing the pads from the nose by the user;

g) removing the pads from the clip by the user;

h) mating one new pad to each of the ends of said clip by the user; and i) repeating steps c) through e).

10. The nostril expansion method as recited in claim 9, wherein the pads each having a central portion and an outer periphery, the central portion having adhesive, the outer portion having no adhesive, the outer portion having a serrated edge, wherein the step of adhering the pads to the nostrils further comprises adhering the central portion of the pads to the nostrils, and wherein the step of removing the pads from the nose further comprises inserting a fingernail under the outer periphery and prying the pad outward.

* * * * *